(12) United States Patent
Leung

(10) Patent No.: US 7,766,948 B1
(45) Date of Patent: Aug. 3, 2010

(54) BONE FIXATION ASSEMBLY

(75) Inventor: Takkwong R Leung, Piscataway, NJ (US)

(73) Assignee: EBI, LLC, Parsippany, NJ (US)

( * ) Notice: Subject to any disclaimer, the term of this patent is extended or adjusted under 35 U.S.C. 154(b) by 496 days.

(21) Appl. No.: 11/124,535

(22) Filed: May 5, 2005

(51) Int. Cl.
*A61B 17/86* (2006.01)
(52) U.S. Cl. .................................. 606/305; 606/291
(58) Field of Classification Search ............ 606/69, 606/72, 73, 280, 289, 291, 305, 315, 316, 606/319; 411/166, 187, 188, 399
See application file for complete search history.

(56) References Cited

U.S. PATENT DOCUMENTS

| | | | | |
|---|---|---|---|---|
| 5,205,694 | A | * | 4/1993 | Nagoshi et al. ............ 411/399 |
| 5,275,601 | A | * | 1/1994 | Gogolewski et al. ........ 606/291 |
| 5,456,719 | A | | 10/1995 | Keller |
| 5,601,553 | A | | 2/1997 | Trebing et al. |
| 5,607,426 | A | * | 3/1997 | Ralph et al. ................ 606/61 |
| 5,709,686 | A | * | 1/1998 | Talos et al. ................ 606/69 |
| 5,772,376 | A | * | 6/1998 | Konig ....................... 411/399 |
| 6,206,881 | B1 | | 3/2001 | Frigg et al. |
| 6,361,537 | B1 | | 3/2002 | Anderson |
| 6,572,622 | B1 | | 6/2003 | Schäfer et al. |
| 6,599,290 | B2 | * | 7/2003 | Bailey et al. .................. 606/69 |
| 6,610,062 | B2 | * | 8/2003 | Bailey et al. .................. 606/61 |
| 6,623,486 | B1 | | 9/2003 | Weaver et al. |
| 6,716,214 | B1 | * | 4/2004 | Jackson ...................... 606/61 |
| 6,730,091 | B1 | * | 5/2004 | Pfefferle et al. .............. 606/70 |
| 7,175,624 | B2 | * | 2/2007 | Konieczynski et al. ........ 606/71 |
| 7,229,442 | B2 | * | 6/2007 | Schafer ..................... 606/272 |
| 2003/0225409 | A1 | * | 12/2003 | Freid et al. ................... 606/69 |
| 2004/0073218 | A1 | * | 4/2004 | Dahners ..................... 606/69 |
| 2004/0127896 | A1 | * | 7/2004 | Lombardo et al. ............ 606/61 |
| 2005/0096657 | A1 | * | 5/2005 | Autericque et al. ........... 606/69 |
| 2005/0101961 | A1 | * | 5/2005 | Huebner et al. ............... 606/72 |
| 2005/0165400 | A1 | * | 7/2005 | Fernandez ................... 606/69 |
| 2006/0004362 | A1 | * | 1/2006 | Patterson et al. ............. 606/69 |

\* cited by examiner

*Primary Examiner*—Eduardo C Robert
*Assistant Examiner*—Tara R George
(74) *Attorney, Agent, or Firm*—Harness, Dickey

(57) ABSTRACT

A bone fixation assembly. The bone fixation assembly includes a fixation member defining at least one aperture, wherein the aperture is adapted for engaging non-threadably and selectively a locking or a non-locking fastener.

8 Claims, 6 Drawing Sheets

BONE FIXATION ASSEMBLY

In certain orthopedic surgical procedures, it is necessary to secure multiple bones or bone portions relative to each other. For example, in spinal surgeries, the fusion of two or more vertebral bodies is required to secure a portion of the spinal column in a desired position. Portions of other bones of the human body can be similarly joined. This need may be the result of physical trauma from fractures or dislocations, degenerative diseases, or tumors.

Various plating systems for internal fixation of various bones are known. Such systems generally include a plate that is attached to the bone or bone portions spanning a fracture line or a spinal disk space. The plate typically includes a plurality of holes through which bone screws are inserted for engaging the bone.

Some plating systems include constrained or locking screws, which are adapted for locking in corresponding plate holes in a fixed orientation. Other plating systems include semi-constrained or non-locking screws, which can be configured to maintain a variable orientation relative to the plate. An example of a plating system that includes constrained and semi-constrained screws is disclosed in currently pending, co-owned U.S. patent application Ser. No. 11/023,096, filed Dec. 22, 2004, the contents of which are incorporated herein by reference. A plating system that includes a locking ring that prevents the screw from backing out of the plate is disclosed in co-owned U.S. Pat. No. 6,599,290, the contents of which are incorporated herein by reference.

Although the existing plating systems can be satisfactory for their intended purposes, there is still a need for new plating systems that are effective and efficient and also provide operative simplicity and versatility to the surgeon.

SUMMARY

The present teachings provide a bone fixation assembly. The bone fixation assembly includes a fixation member defining at least one aperture. The aperture is adapted for engaging non-threadably and selectively a locking or a non-locking fastener.

In one aspect the present teachings provide a bone fixation assembly that includes at least one locking fastener including a locking head integral thereon, at least one non-locking fastener including a non-locking head integral thereon, and a fixation member defining at least one aperture. The aperture is adapted for receiving selectively and non-threadably any one of the locking or non-locking fasteners.

The present teachings also provide a method for securing a first bone portion to a second bone portion. The method includes providing a fixation member defining a plurality of apertures including a first aperture having a compression feature, wherein each aperture is adapted for engaging non-threadably and selectively a locking or a non-locking fastener, positioning the fixation member adjacent the bone portions, inserting a locking fastener through the first aperture into one of the first and second bone portions, guiding the locking fastener along the compression feature for bone compression, and locking the locking fastener relative to the fixation member.

The present teachings also provide a bone fixation kit that includes a plurality of locking fasteners, a plurality of non-locking fasteners, and at least one fixation member defining a plurality of apertures. At least one of the apertures is adapted for receiving selectively and non-threadably any one of the locking or non-locking fasteners.

Further areas of applicability of the present invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description is merely exemplary in nature and is in no way intended to limit the invention, its application, or uses. For example, the present teachings can be used for, but are not limited to, fusion procedures of adjoining bones, such as vertebrae, and/or for internal fixation of fractures in any bones.

Figure 1:
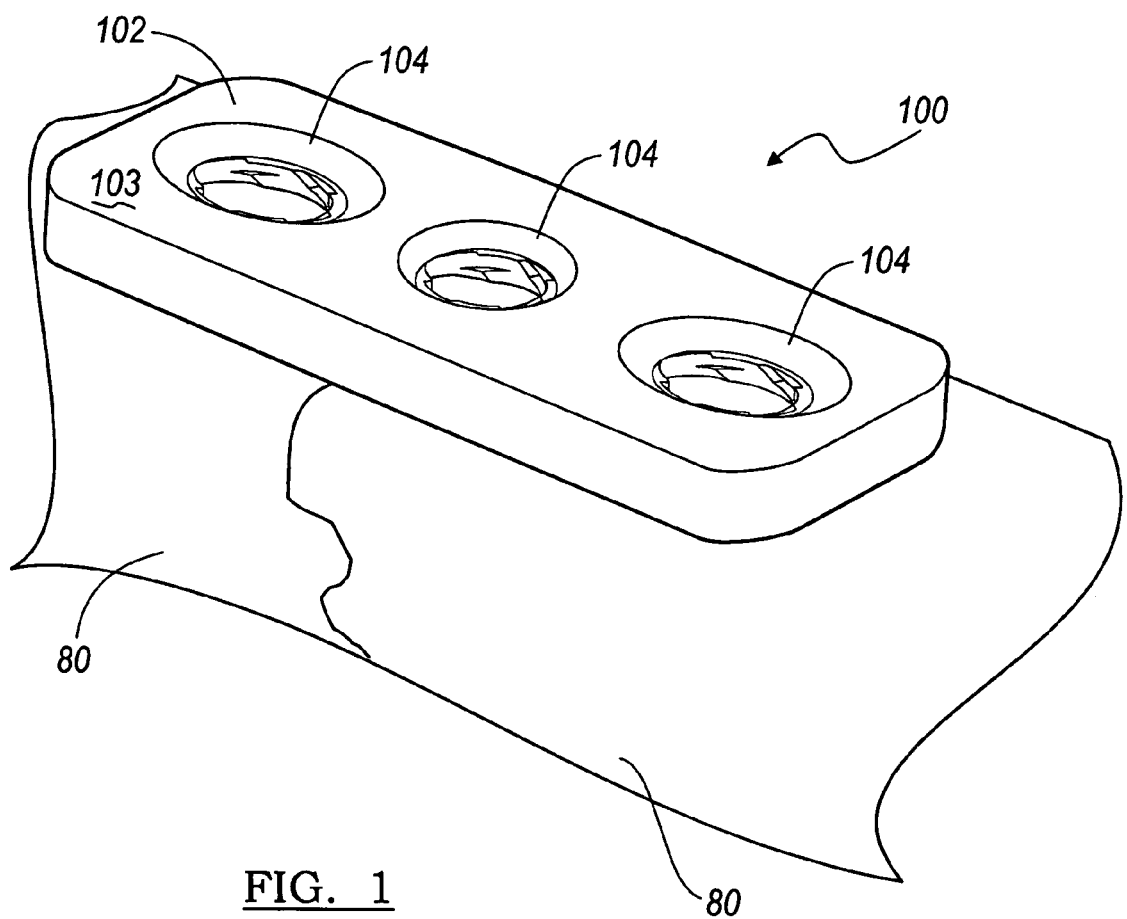
FIG. 1 is an environmental and perspective view of a bone fixation assembly according to the present teachings, the bone fixation assembly shown operatively associated with a bone.
Figure 2:
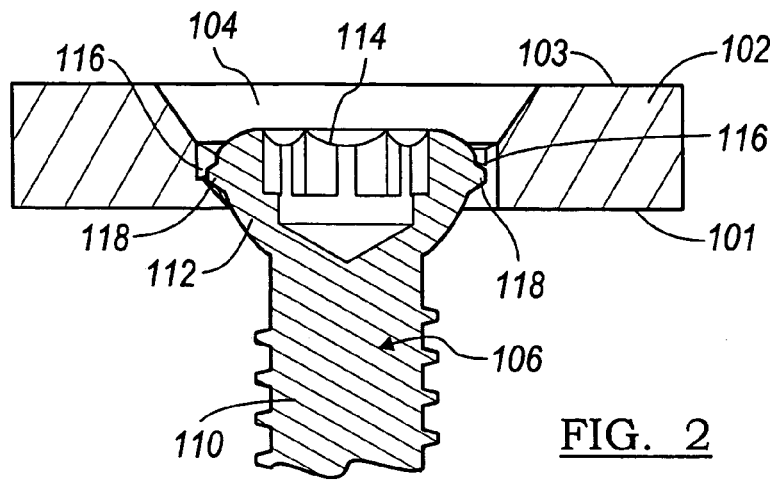
FIG. 2 is a sectional view of a bone fixation assembly illustrating a locking fastener according to the present teachings.
Figure 3:
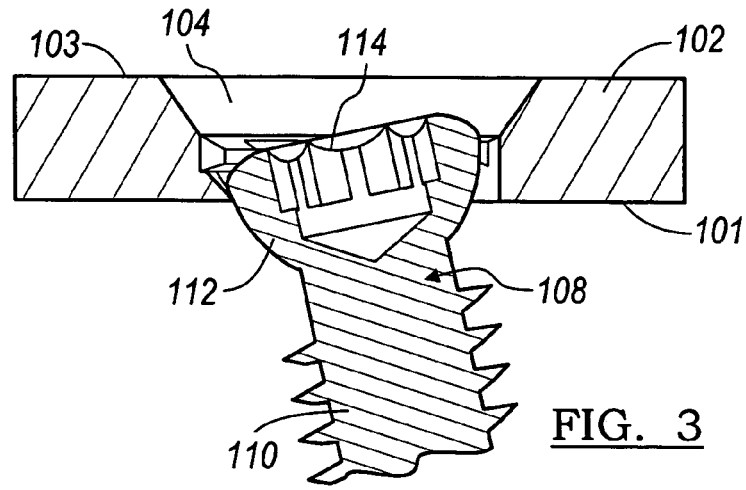
FIG. 3 is a sectional view similar to FIG. 2 illustrating a non-locking fastener according to the present teachings.
Figure 4:
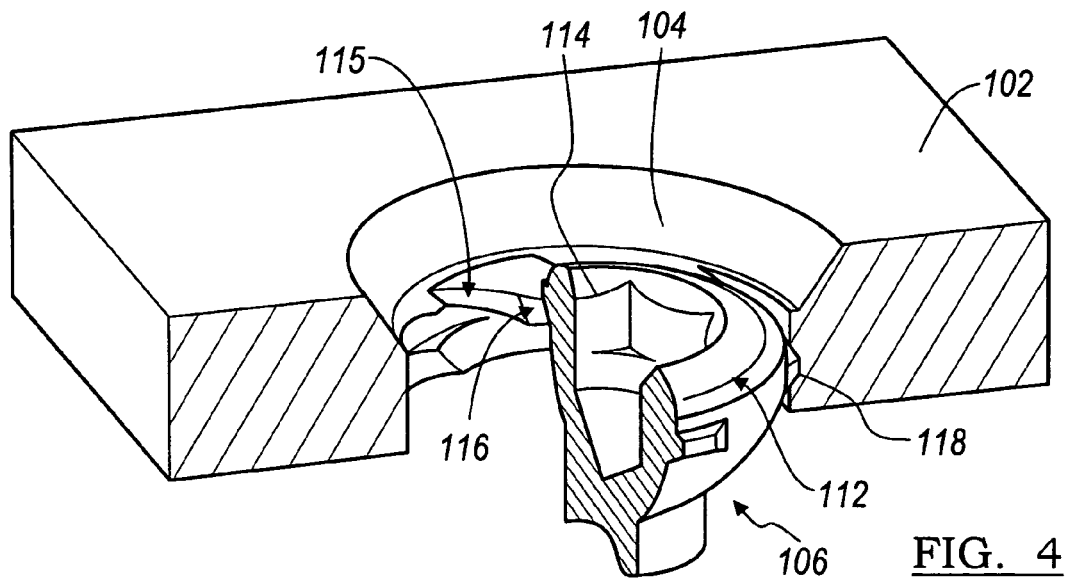
FIG. 4 is a partially cut-away perspective view of a bone fixation assembly illustrating a locking fastener according to the present teachings.
Figure 5:
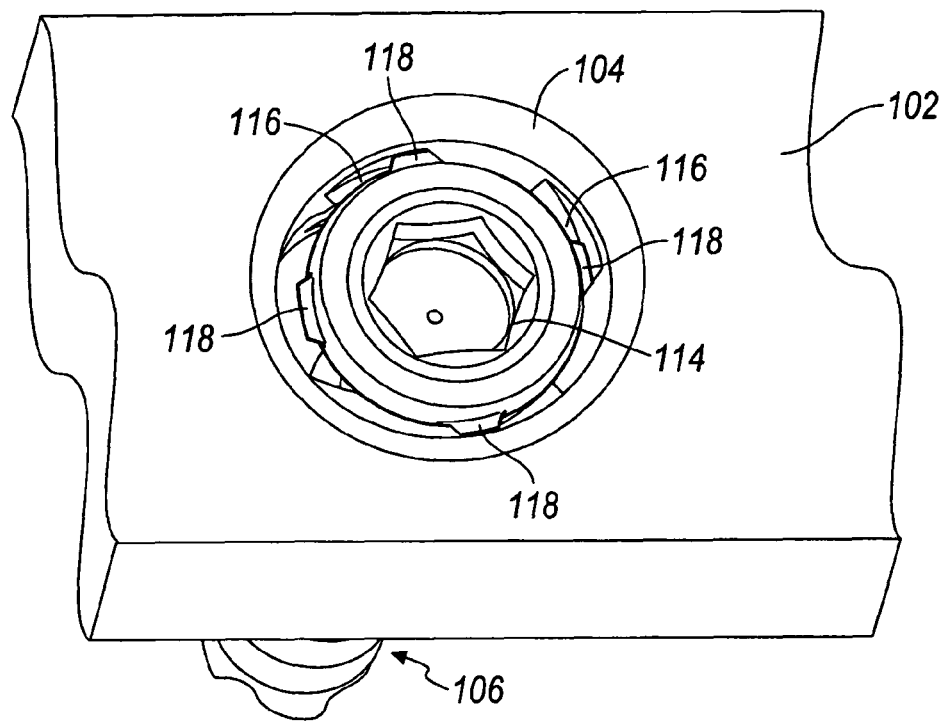
FIG. 5 is a top perspective view of a bone fixation assembly with a locking fastener according to the present teachings.

Referring to FIG. 1, an exemplary bone fixation assembly 100 according to the present teachings is illustrated in internal fixation of two bones or bone portions 80. Referring to FIGS. 1-3, the bone fixation assembly 100 includes a fixation member 102 that has a bone engagement surface 101 and an opposite, non-engagement surface 103. The fixation member 102 can be a substantially planar plate or planar bar, or can be a substantially curved shell that has an anatomically adapted shape. The fixation member 102 has generally a dimension spanning the opposing surfaces 101, 103 ("thickness"), such that the thickness of the fixation member 102 is substantially smaller that at least another dimension of the fixation member 102, such as a width or length of the fixation member 102. The thickness of the fixation member 102 can be variable.

The fixation member 102 can have one or more apertures 104 therethrough. At least one aperture 104 can be adapted for receiving selectively a locking fastener 106 or a non-locking fastener 108. Further, any of the apertures 104 can be adapted for compression locking, as will be discussed below in connection with FIGS. 9-12. Each of the locking and non-locking fasteners 106, 108 can include a shaft 110 and a head 112 integrally or modularly connected with the shaft 110. The shaft 110 can include a threaded portion for bone engagement and a head formation 114, such as a hex formation, for example. The head formation 114 is adapted for engagement with a driver or other insertion or extraction tool (not shown) in a conventional manner.

Referring to FIGS. 2, 4, 5, 7 and 8, the aperture 104 can include a non-threadable locking mechanism 115. The non-threadable locking mechanism 115 can include, for example, one or more locking grooves 116 configured for locking engagement with corresponding locking tabs 118 that extend from the head 112 of the locking fastener 106. Each locking groove 116 can have variable radius. In one aspect, the radius of the locking groove 116 decreases clockwise (as viewed from the non-engagement surface 103), such that clockwise rotation of the locking fastener 106 relative to the fixation member 102 guides the locking tabs 118 into locking engagement with the corresponding locking grooves 116 and locks the locking fastener 106 relative to the fixation member 102. The locking tabs 118 can be tightly engaged with the locking grooves 116 for preventing back-out of the locking fasteners 106. Although four locking grooves 116 and tabs 118 are illustrated herein, it will be appreciated that a different number of locking grooves 116 and tabs 118 can be used. Four locking grooves 116 and tabs 118, for example, may provide greater degree of locking stability relative to a lesser number.

In the locked position illustrated in FIG. 2, the shaft of the locking fastener 106 can be oriented substantially perpendicularly to the engagement surface 101. It will be appreciated, however, that locking fastener 106 can be retained in an unlocked position, in which the tabs 118 are not engaged with the locking grooves 116, such that the shaft 110 of the locking fastener 106 can angulate relative to the engagement surface 101 within a cone of angulation which is determinable by the specific dimensions and geometry of the aperture 104 and the locking fastener 106. In one application, the cone of angulation defines an angle of approximately 18° from an axis perpendicular to the fixation member 102.

Figure 6:
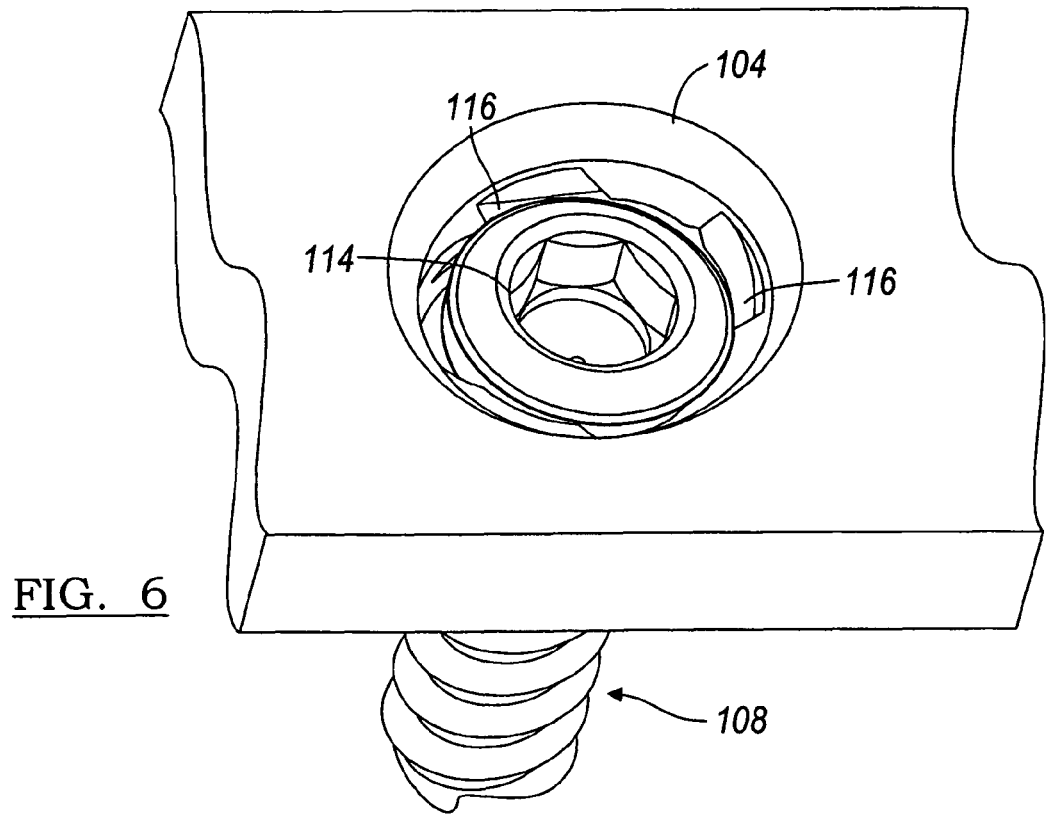
FIG. 6 is a perspective view of a bone fixation assembly illustrating a non-locking fastener according to the present teachings.
Figure 7:
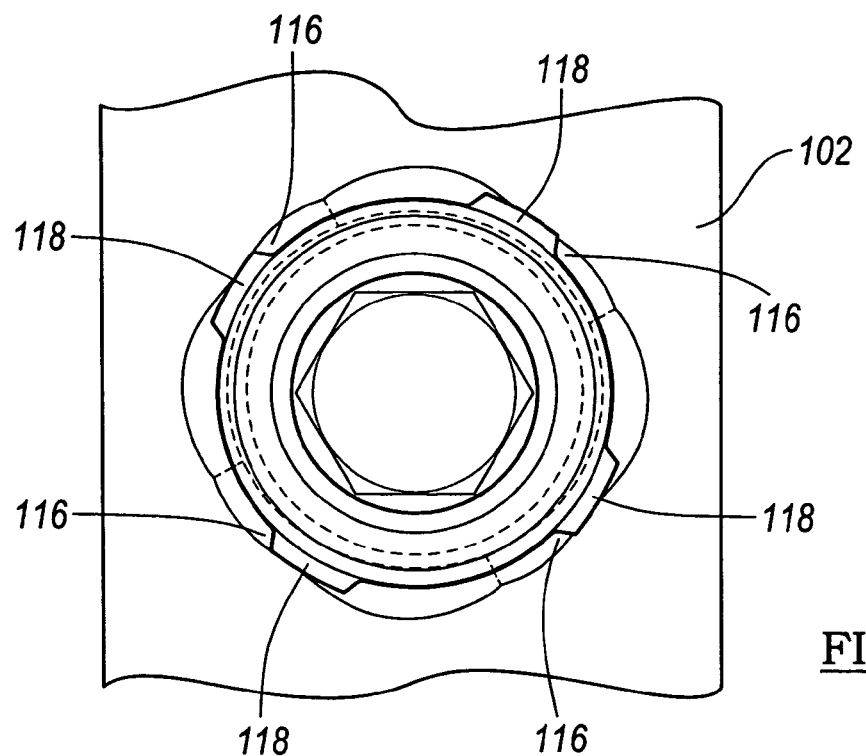
FIG. 7 is a top view of a bone fixation assembly illustrating a locking fastener according to the present teachings.
Figure 8:
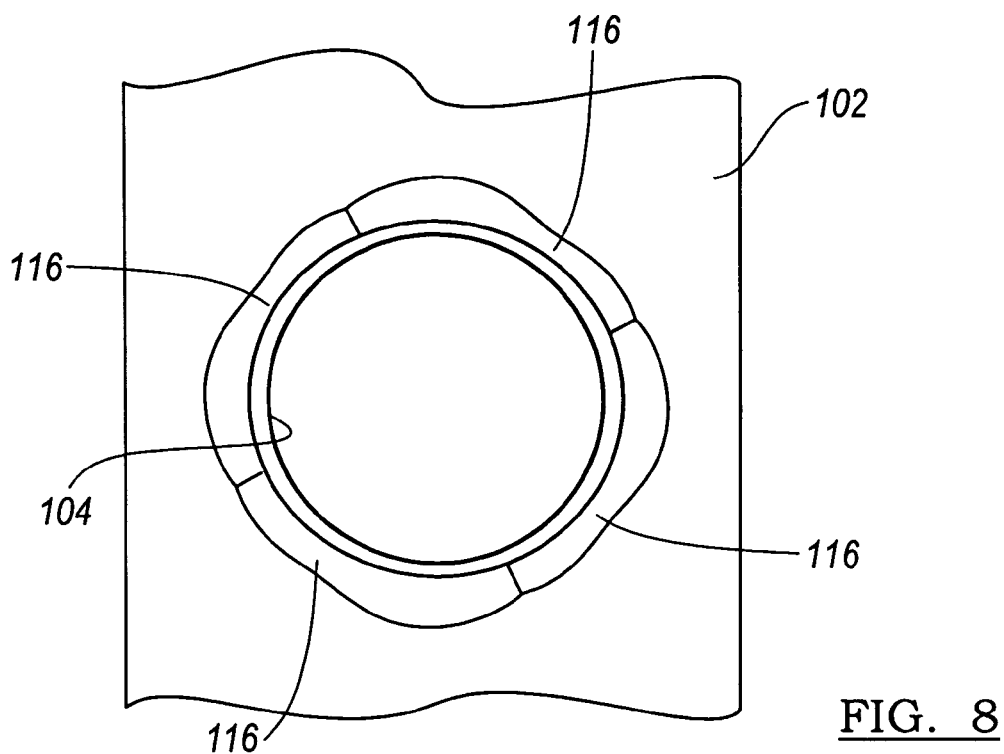
FIG. 8 is a top view of a bone fixation assembly illustrating an aperture according to the present teachings.

Referring to FIGS. 3 and 6, the non-locking fastener 108 can be received in the same aperture 104. The shaft 110 of the non-locking fastener 108 can angulate relative to the engagement surface 101 within a cone of angulation which is also determinable by the specific dimensions and geometry of the aperture 104 and the non-locking fastener 108.

Figure 9:
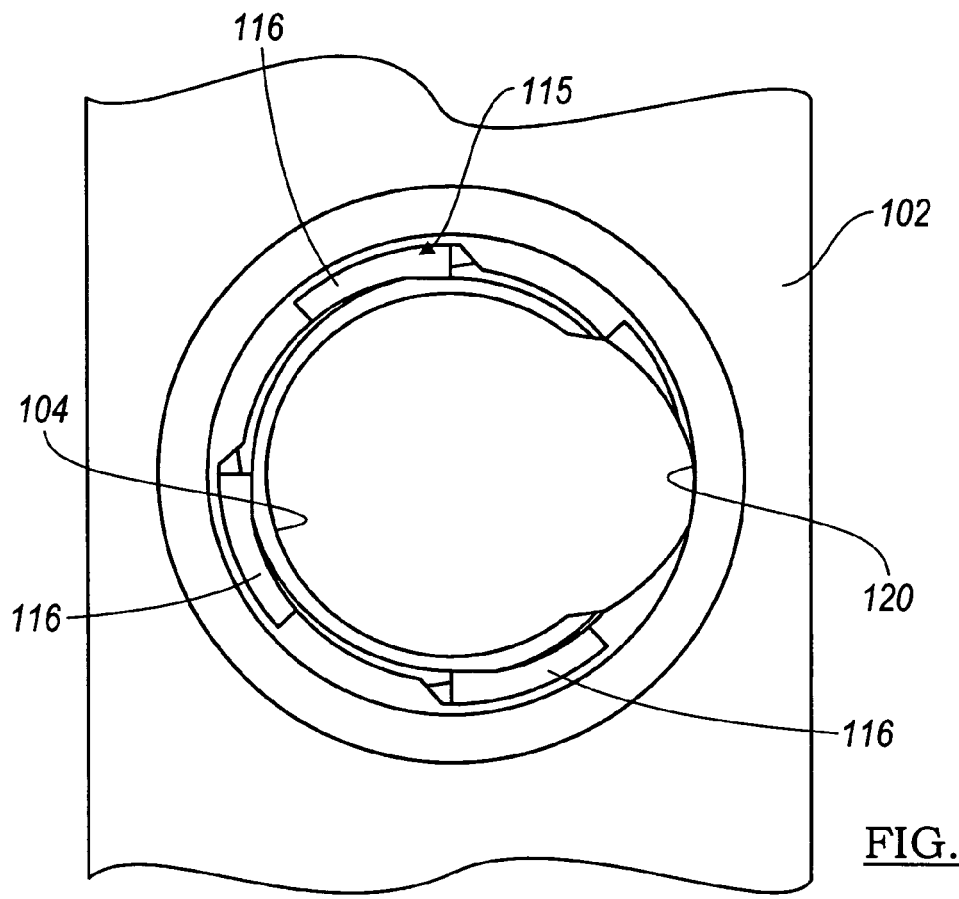
FIG. 9 is a plan view of a bone fixation assembly illustrating an aperture with a compression feature according to the present teachings.
Figure 10:
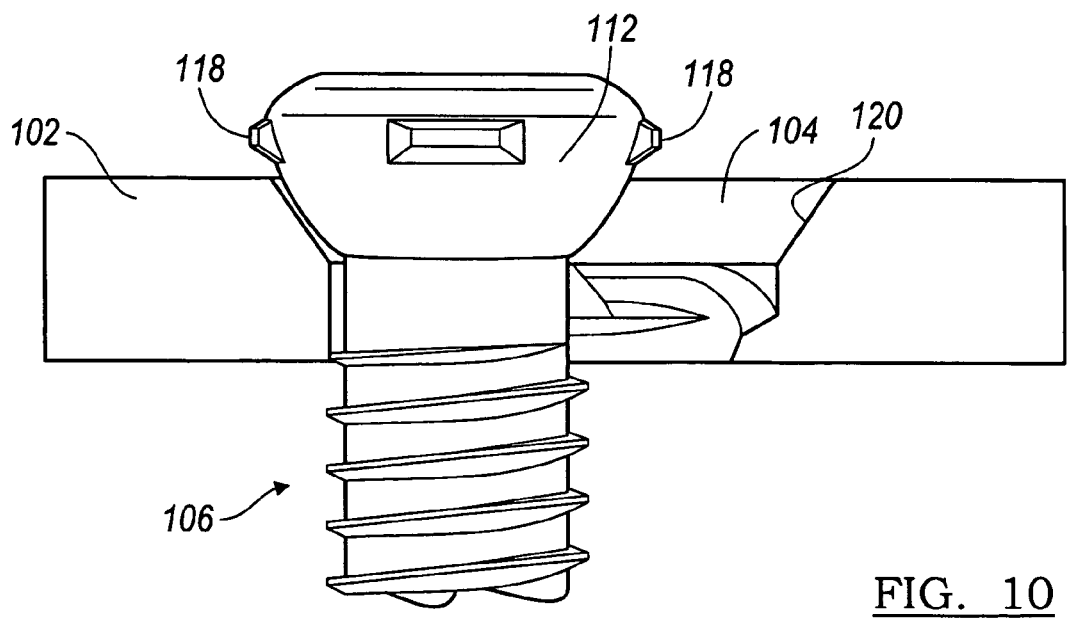
FIGS. 10-12 illustrate stages in a compression and locking procedure for a fixation assembly according to the present teachings.
Figure 11:
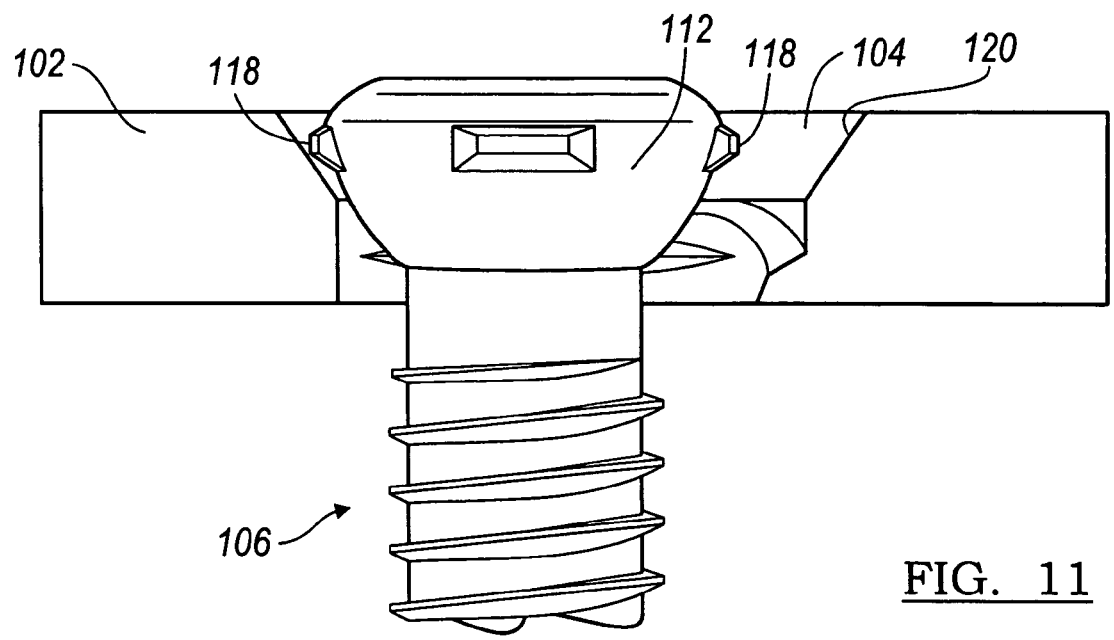
Figure 12:
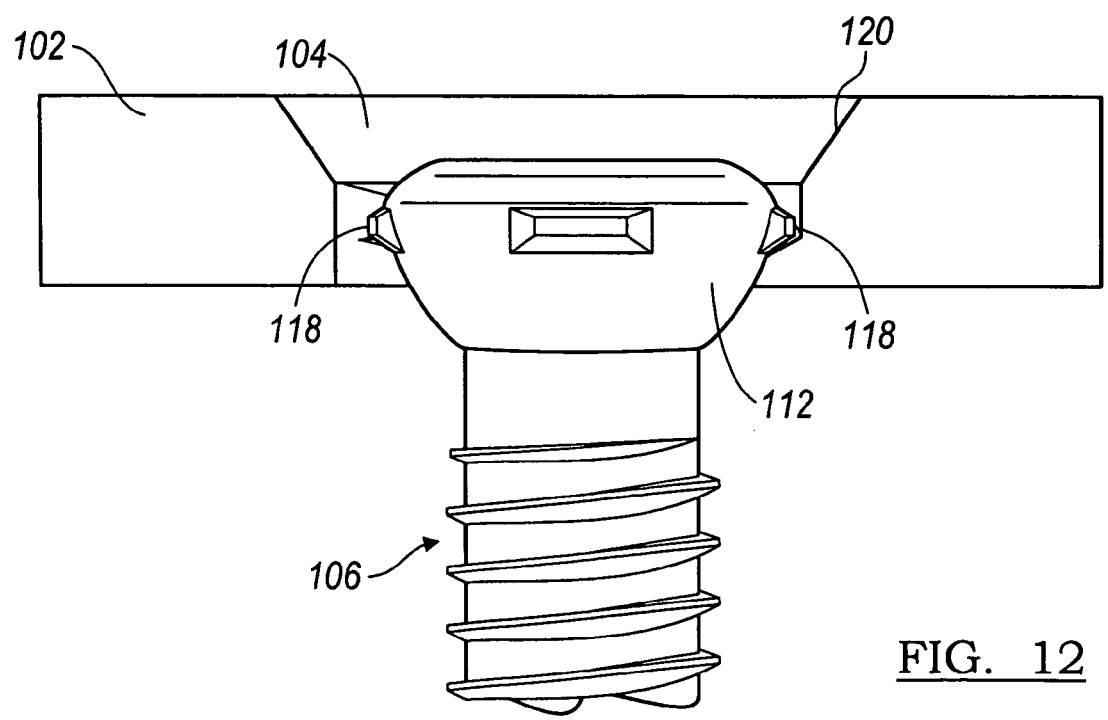

Referring to FIG. 9, the aperture 104 can also include a compression feature 120 for compressing two bones or bone fragments 80 against or closer to each other. The compression feature 120 can be, for example, a compression ramp and/or an elongated slot or extension of the aperture 104. Referring to FIGS. 10-12, an exemplary compression and locking procedure according to the present teachings is illustrated. The locking fastener 106 is inserted into the aperture 104, as shown in FIG. 10. The head 112 of the locking fastener 106 is then rotated using a driver, causing the locking fastener 106 to follow the compression feature 120 and start bone compression, as illustrated in FIG. 11. Further rotation causes the locking fastener 106 to lock relative to the fixation member 102, as illustrated in FIG. 12. It will be understood that, although the locking fastener 106 is illustrated in the exemplary compression procedure, a non-locking faster 108 can also be used to effect bone compression.

The fixation assembly 100 of the present teachings can also be provided as kit including one or more fixation members 102 with different shapes and configuration and/or sizes for the fixation member 102 and the apertures 104 for different applications, different size locking fasteners 106, and different size non-locking fasteners 108. The kit affords the surgeon flexibility to select the appropriate combination of fixation members 102 and locking or non-locking fasteners 106, 108 with or without compression, as needed for a particular procedure. Further, the configuration of the locking mechanism 115 permits easy locking without compression or after compression. The locking mechanism 115 avoids complementary threading between the locking fastener 106 and the aperture 104 of the fixation member 102, and known disadvantages associated with threading, such as spending time and effort for proper alignment for threading and risk of thread failure.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A bone fixation assembly comprising:
a fixation member;
at least one aperture formed through said fixation member;
at least two locking features circumferentially spaced around an inner perimeter of said at least one aperture and including a first end, a second end, and a ramp extending between said first end and said second end, said first end being open in a direction substantially parallel to an axis extending through said at least one aperture and said second end including a groove having a longitudinal axis formed substantially perpendicular to said axis extending through said at least one aperture; and
a fastener received within said at least one aperture and including at least two discrete locking members extending from said fastener and respectively received in said at least two locking features, said at least two locking members being circumferentially spaced around an outer perimeter of said at least one fastener and received within said first end in an unlocked state and received within said groove of said second end in a locked state to restrict removal of said fastener from said at least one aperture.

2. The bone fixation assembly of claim 1, wherein said at least two discrete locking members are disposed substantially in the same plane, said plane extending substantially perpendicular to a longitudinal axis of said fastener.

3. The bone fixation assembly of claim 1, wherein said first end of said at least two locking features includes a different radius than said second end of said at least two locking features.

4. The bone fixation assembly of claim 1, wherein said first end of said at least two locking features includes a greater radius than said second end of said at least two locking features.

5. The bone fixation assembly of claim 1, wherein said first ends of said at least two locking features are disposed substantially in the same plane, said plane extending substantially perpendicular to a longitudinal axis of said fastener.

6. The bone fixation assembly of claim 1, wherein said second ends of said at least two locking features are disposed substantially in the same plane, said plane extending substantially perpendicular to a longitudinal axis of said fastener.

7. The bone fixation assembly of claim 1, further comprising a compression feature receiving said fastener and operable to cooperate with said fastener to apply a force to at least one bone in a direction substantially perpendicular to an axis extending through said at least one aperture.

8. The bone fixation assembly of claim 7, wherein said compression feature includes at least one of a ramp and an increased radius portion of said at least one aperture.

* * * * *